（12) United States Patent
Nygard et al.

(10) Patent No.: US 8,588,911 B2
(45) Date of Patent: Nov. 19, 2013

(54) MEDICAL IMPLANT WITH CURRENT LEAKAGE CIRCUITRY

(75) Inventors: Tony Mikael Nygard, Terrigal (AU); Kostas Tsampazis, North Ryde (AU); Marcus Ignacio, Macquarie University (AU); Paul Carter, West Pennant Hills (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/238,532

(22) Filed: Sep. 21, 2011

(65) Prior Publication Data

US 2013/0073002 A1 Mar. 21, 2013

(51) Int. Cl.
*A61N 1/37* (2006.01)
(52) U.S. Cl.
USPC .............................. 607/27; 607/63; 607/115
(58) Field of Classification Search
USPC .................................. 607/27–29, 36, 37, 63
See application file for complete search history.

(56) References Cited

U.S. PATENT DOCUMENTS

| 4,532,930 | A |   | 8/1985  | Crosby et al. |         |
|-----------|---|---|---------|---------------|---------|
| 4,584,635 | A |   | 4/1986  | MacInnis et al. |       |
| 5,481,194 | A |   | 1/1996  | Schantz et al. |        |
| 5,741,311 | A | * | 4/1998  | Mc Venes et al. | 607/28 |
| 5,824,016 | A |   | 10/1998 | Ekwall        |         |
| 5,910,156 | A | * | 6/1999  | Cinbis et al. | 607/27  |
| 5,999,849 | A |   | 12/1999 | Gord et al.   |         |
| 6,011,398 | A |   | 1/2000  | Bald et al.   |         |
| 6,096,062 | A |   | 8/2000  | Silvian       |         |
| 6,144,881 | A |   | 11/2000 | Hemming et al. |        |
| 6,358,281 | B1|   | 3/2002  | Berrang et al. |        |
| 6,542,777 | B1|   | 4/2003  | Griffith et al. |       |
| 6,760,624 | B2| * | 7/2004  | Anderson et al. | 607/28 |
| 7,454,249 | B1| * | 11/2008 | Bornzin et al. | 607/27 |
| 7,574,259 | B1| * | 8/2009  | Pei et al.    | 607/28  |
| 7,623,929 | B1|   | 11/2009 | Griffith      |         |
| 7,904,174 | B2| * | 3/2011  | Hammill et al. | 607/116|
| 7,962,222 | B2|   | 6/2011  | He et al.     |         |
| 2005/0024245 | A1 |  | 2/2005 | Sit et al.   |         |
| 2005/0225909 | A1 |  | 10/2005 | Yoshizaki et al. |    |
| 2005/0237680 | A1 |  | 10/2005 | Egner       |         |

(Continued)

FOREIGN PATENT DOCUMENTS

EP 0479099 8/1992
JP 2003315374 11/2003

(Continued)

OTHER PUBLICATIONS

International Search Report for International Application No. PCT/AU2007/001224 mailed Sep. 18, 2007 (2 pages).

(Continued)

*Primary Examiner* — Brian T Gedeon
(74) *Attorney, Agent, or Firm* — Kilpatrick, Townsend & Stockton, LLP.

(57) ABSTRACT

Medical device implants for stimulating the nervous system of a recipient are disclosed. Embodiments include a cochlear implant with electrodes for delivering charge to the cochlea of the recipient and stimulation circuitry for delivering the charge to the electrodes. The medical devices include a transfer line which carries power and/or communication signals, the transfer line being in contact with tissue of the recipient when the medical device implant is implanted. A leakage capture conductor and/or sensing electrode is located or locatable proximate the insulated conductor.

13 Claims, 5 Drawing Sheets

(56) References Cited

U.S. PATENT DOCUMENTS

| | | |
|---|---|---|
| 2006/0187594 A1 | 8/2006 | DiSalvo |
| 2006/0247684 A1 | 11/2006 | Halperin et al. |
| 2007/0255352 A1* | 11/2007 | Roline et al. .................... 607/63 |
| 2007/0265686 A1 | 11/2007 | Greenberg et al. |
| 2008/0071168 A1 | 3/2008 | Gauglitz et al. |
| 2008/0154342 A1 | 6/2008 | Digby et al. |
| 2009/0118805 A1 | 5/2009 | Greenberg et al. |
| 2010/0023084 A1* | 1/2010 | Gunderson .................... 607/28 |
| 2010/0249644 A1 | 9/2010 | Miles et al. |
| 2010/0274319 A1 | 10/2010 | Meskens |
| 2011/0178575 A1 | 7/2011 | Cryer et al. |
| 2011/0208269 A1 | 8/2011 | He et al. |
| 2012/0191160 A1* | 7/2012 | Moghe et al. .................... 607/57 |

FOREIGN PATENT DOCUMENTS

| | | |
|---|---|---|
| WO | 9534824 | 12/1995 |
| WO | 97/01314 | 1/1997 |
| WO | 2006/124481 | 11/2006 |
| WO | 2008022404 | 2/2008 |
| WO | 2009/127014 | 10/2009 |
| WO | 2010000027 | 1/2010 |
| WO | 2013042068 | 3/2013 |

OTHER PUBLICATIONS

International Search Report and Written Opinion for International Application No. PCT/IB2012/055003 mailed Mar. 15, 2013 (10 pages).

* cited by examiner

MEDICAL IMPLANT WITH CURRENT LEAKAGE CIRCUITRY

BACKGROUND

Field of the Invention

The present invention relates to the field of medical implants for stimulating the nervous system of a recipient, the medical implants including implantable components and a power and/or signal transfer line between implantable components.

One form of medical implant for stimulating the nervous system of a recipient is a cochlear implant. A cochlear implant includes an implant component and an array of electrodes. The implant component is designed to deliver a stimulating signal over a transfer line to the electrodes. The transfer line is typically a cable with a number of insulated conductors corresponding to the number of electrodes in the array. The electrodes deliver charge of the stimulating signal to the cochlea, to excite the auditory nerves of the recipient of the cochlear implant.

To evoke a hearing-like sensation with a particular apparent loudness of intensity, the cochlear implant must deliver a time-constrained, minimum level of electric charge. A known issue with cochlear implants is the requirement that the net charge delivered to each electrode remain close to zero in order to prevent non-reversible galvanic reactions, electrode corrosion and the creation of chemical species injurious to adjacent cells and body tissue. Various methods have been proposed to address this problem, including the use of direct current blocking capacitors connected in series with the electrodes or particular switching arrangements, which may for example periodically short circuit electrodes to dissipate any accumulated charge.

A cochlear implant may include other potential sources of electric charge that may result in a risk of adverse affects and/or reduced performance. Any power and/or signal transfer line between component parts of the cochlear implant may be a source of leakage current, for example if the insulation around the transfer line fails or if insulation around a connection of the transfer line fails. In addition, for neural stimulation, it may be important that the signal provided to the electrodes is clear and any irregular stimulation signals are minimised or eliminated.

SUMMARY

The invention generally relates to medical device implants for stimulating the nervous system of a recipient. Some of the disclosed embodiments include a cochlear implant with electrodes for delivering charge to the cochlea of the recipient and stimulation circuitry for delivering the charge to the electrodes.

The medical devices include a transfer line which carries power and/or communication signals, the transfer line being in contact with tissue of the recipient when the medical device implant is implanted. A leakage capture conductor and/or sensing electrode is located or locatable proximate the insulated conductor. In some embodiments the leakage capture conductor and sensing electrode are distinct, and in others they are the same component.

The leakage capture conductor is connected to a low impedance voltage reference, so as to carry leakage current from the transfer line to the low impedance voltage reference, as an alternative to the leakage current being carried in the recipient's tissue. In a cochlear implant, the voltage provided by the voltage reference may be selected to be between a maximum and minimum voltage applied to the cochlea by the electrodes.

A switching circuit for delivering charge to the electrodes may be arranged so that when an electrode is connected to either the first power supply rail or the second power supply rail, current sources may be interposed between the power supply rails and the electrode, whereby the current sources provide high impedance connections. The provision of a high impedance source for the electrodes may reduce distortion in the stimulation signal provided by the implant in the event that there is leakage current from the transfer line.

In some embodiments, the leakage capture conductor is located outside the transfer line so as to be in electrical contact with said tissue of the recipient when the medical device implant is implanted.

In some embodiments, the transfer line may carry a power signal from a power module housing a battery to a stimulation module housing the stimulation circuitry. The power signal may be an alternating current signal. Direct current blocking capacitors may be provided in series with the transfer line. In other embodiments, the leakage capture conductor is embedded in the insulation of the insulated conductor so as to be insulated from surrounding tissue when the medical device implant is implanted in a recipient. In these other embodiments, the leakage capture conductor may be switched between a function of delivering leakage current to the low impedance voltage reference and a function of delivering leakage current to a current detector.

The sensing electrode may be embedded in insulation of the transfer line and connected to a current detection circuit, which detects current between a point of failure of said insulation and an electrode. The electrode may be an electrode for stimulating the nervous system of the recipient or a diagnostic electrode connected to a switching circuit for testing for the presence of leakage current.

Further embodiments will become apparent from the following description, given by way of example and with reference to the accompanying drawings.

BRIEF DESCRIPTION OF THE DRAWINGS

By way of example only, preferred embodiments of the invention are now described with reference to the accompanying drawings, in which.

DETAILED DESCRIPTION

The following description is given with reference to various embodiments of the present invention. These various embodiments are described in connection with a cochlear implant, however, embodiments of the present invention, such as those providing a path for leakage current and/or detecting leakage current, may be applied to other medical implant devices that include a power and/or signal transfer line.

Figure 1:
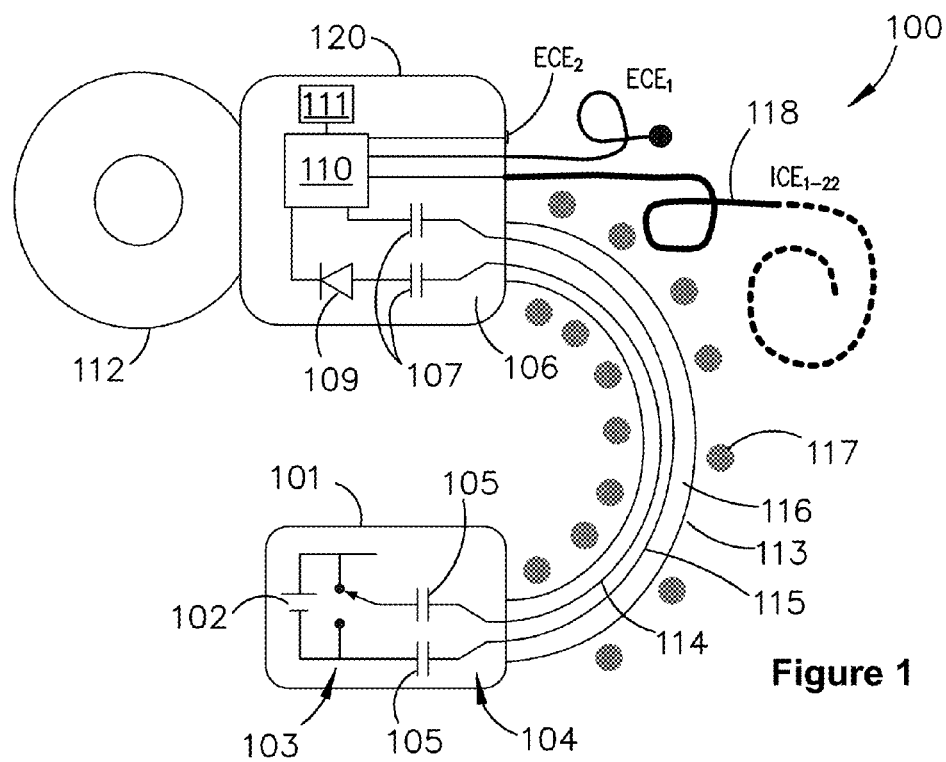
FIG. 1 shows a schematic representation of a cochlear implant including a leakage capture conductor in accordance with an embodiment of the present invention.

FIG. 1 shows a diagrammatic representation of an embodiment of a cochlear implant 100. The cochlear implant 100 includes a power source module 101 and a stimulator module 120.

The power source module 101 includes a battery 102 and an inverter 103 for providing at a signal output 104 an AC power signal. The inverter 103 may for example be an integrated circuit including an H-bridge switch configuration. The signal output 104 includes DC blocking capacitors 105.

The stimulator module 120 includes a signal input 106, for receiving the AC power signal from the power source module 101. In some embodiments the signal input 106 may also be used as a signal input/output, the signal for example being generated by modulating/coding a signal onto the AC carrier. The signal input 106 includes two DC blocking capacitors 107. A rectifier 109 is connected to the signal input 106 for converting the AC power signal into a DC supply signal comprising a positive voltage signal $V_{DD}$ and a negative voltage signal $V_{SS}$, provided over supply rails.

The positive voltage signal $V_{DD}$ and a negative voltage signal $V_{SS}$ are received by a switching circuit 110, which controls the supply of current to and from stimulation electrodes $ICE_{1-22}$ and a reference electrode $ECE_1$. The number of stimulation electrodes and reference electrodes is a matter of design choice and may vary between implementations. For example, as smaller electrodes and/or conductors for the transfer lines to the electrodes are used, then the number of stimulation electrodes may increase. In the embodiment shown in FIG. 1, a second reference electrode $ECE_2$ is provided, which may provide redundancy for the reference electrode $ECE_1$ and/or may be used as a sensing electrode, for example to provide for neural response telemetry.

The stimulator module 120 includes a controller 111. References to the controller 111 include both implementations as a single integrated circuit microcontroller and a plurality of microcontrollers, each with assigned functions and with optional redundancy. One function of the controller 111 is to implement a control function to receive signals at a pickup coil 112 and, in response control the switching circuit 110 to provide current to the stimulation electrodes $ICE_{1-22}$ and the reference electrode $ECE_1$ as required.

The AC power signal is communicated from the signal output 104 to the signal input 106 over a transfer line in the form of an insulated cable 113. The insulated cable 113 includes a pair of wires 114, 115 for carrying the AC power signal and a reference voltage and insulation 116 about the wires 114, 115. A leakage capture conductor 117 is provided so as to be located or locatable proximate the insulated cable 113 so as to be in electrical contact with tissue of the recipient of the implant. For example, the leakage capture conductor 117 may be a wire coiled around the outer surface of the insulated cable 113, optionally bonded to the insulated cable 113 through an adhesive, tie or otherwise. In other embodiments the leakage capture conductor 117 may be a mesh located around the insulation 116. More generally, the leakage capture conductor is any conductor positioned or positionable near the cable between the potential source of leakage current and the electrodes ICE, ECE.

In other embodiments the leakage capture conductor 117 may be a wire, mesh or other structure of conductive material embedded within the insulation 116. When the leakage capture conductor 117 is within the insulation 116, the insulation extends between the leakage capture conductor 117 and the wires 114, 115 to provide adequate insulation so as to not adversely affect the communication of the AC power signal during normal operation. Embedding the leakage capture conductor 117 may allow it to be used for more than one purpose, as explained below. However, it is expected that the performance of the leakage capture conductor 117 to capture leakage current may be less than optimum when it is not in electrical contact with the surrounding tissue of the recipient of the implant.

The leakage capture conductor 117 may, for example, be made of platinum. Other suitable conductive materials may be used, having regard to the conductivity of the material, strength of the material and other factors, such as ease and cost of manufacture.

Figure 2:
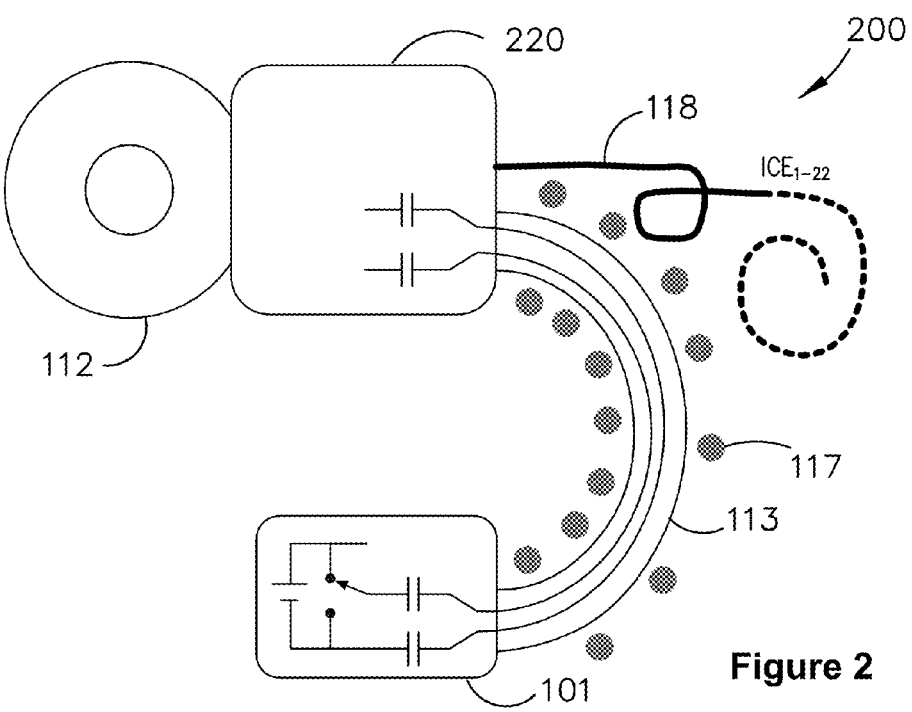
FIG. 2 shows a schematic representation of a cochlear implant including an a leakage capture conductor in accordance with another embodiment of the present invention.

FIG. 2 shows a schematic representation of another embodiment of a cochlear implant 200. The cochlear implant 200 has a similar structure to the cochlear implant 100, including the same power source module 101, insulated cable 113 and leakage capture conductor 117. The stimulator module 220 performs a like function to the stimulator module 120 described above, but implements a bipolar stimulation strategy, not involving a separate reference electrode, when providing the stimulation signals.

Figure 3:
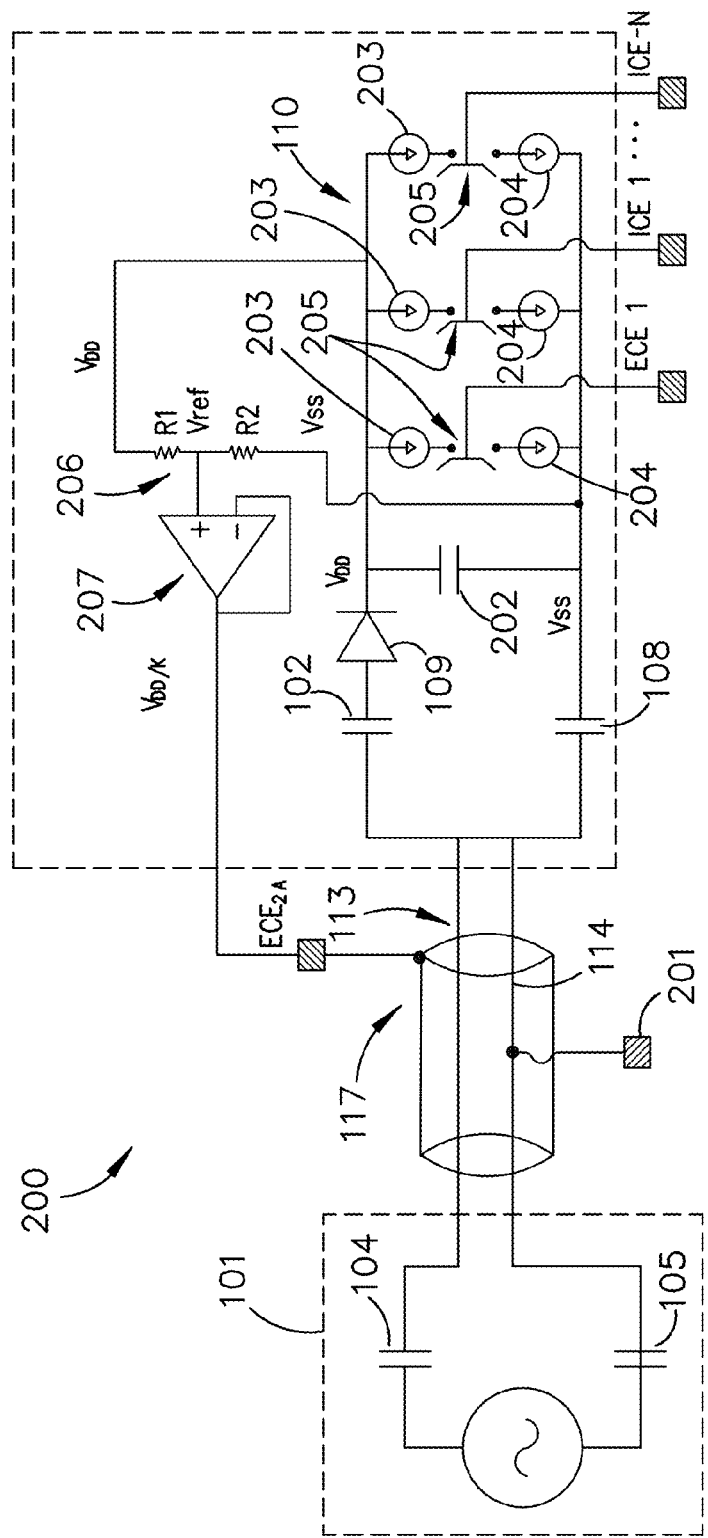
FIG. 3 shows a circuit diagram of a cochlear implant including a leakage capture conductor in accordance with an embodiment of the present invention.

FIG. 3 shows a circuit diagram of an embodiment of circuitry 200 of the cochlear implant 100 shown in FIG. 1 and like reference numerals have been used for like components between FIGS. 1 and 3. The power source module 101 provides an AC signal having a DC voltage component regulated by the voltage of the surrounding tissue. A reference electrode 201 (which was not shown in FIG. 1) for providing a reference voltage for the AC signal is provided for implantation in the tissue of the recipient, the reference electrode 201 being connected to the wire 114 of the insulated cable 113 (the insulation 116 is not shown in FIG. 3). The AC signal is received by the rectifier 109, which provides a DC signal output across a smoothing capacitor 202, the DC signal consisting of $V_{DD}$ and $V_{SS}$ provided to the switching circuit 110 on supply rails, for convenience also referred to as $V_{DD}$ and $V_{SS}$.

The switching circuit 110 includes a plurality of current sources 203 connected to $V_{DD}$ and a plurality of current sources connected to $V_{SS}$, so that the current sources 203 and 204 can operate in a push/pull arrangement when providing stimulation signals either between pairs of the stimulation electrodes $ICI_{1-22}$ (bipolar stimulation) or between a stimulation electrode $ICI_{1-22}$ and the reference electrode $ECE_1$ or the reference electrode $ECE_2$ (monopolar stimulation). The stimulation signals are commenced and ended by switches 205 operated according to a switching strategy. The switching strategy is a design consideration and as mentioned herein above a typical switching strategy is for the controller 111 (not shown in FIG. 3) to control the switches 205 to provide a biphasic pulse to the electrodes. Examples of other types of pulses that form an alternating current signal and which may be provided by the switches 205 include triphasic pulses or asymmetrical pulses. The stimulation electrodes $ICI_{1-22}$ are connected between the current sources, as is the reference electrode $ECE_1$.

A voltage divider 206 is provided between $V_{DD}$ and $V_{SS}$. In the embodiment shown in FIG. 3 the voltage divider is provided by two large resistors R1, R2. The voltage divider provides a DC reference voltage $V_{ref}$. The magnitude of the reference voltage $V_{ref}$ is dependent on the stimulation strategy used, but a reference voltage $V_{ref}=V_{DD}/2$ is $V_{SS}=0$ or $(V_{DD}-V_{SS})/2+V_{SS})$ if $V_{SS}\neq 0$ may suit a typical symmetrical biphasic pulse stimulation signal. If the stimulation strategy is a triphasic pulse or other stimulation strategy that provides an asymmetrical pulse, then a suitable reference voltage $V_{ref}$ is the mid point between the peak voltages provided on the forward and reverse current pulses, or if there are a plurality of forward current pulses and/or a plurality of reverse current pulses, at a mid point between the maximum voltage pulses.

The output $V_{ref}$ from the voltage divider 206 is provided to a low impedance node 207. In the example shown in FIG. 3, the low impedance node 207 is a voltage buffer. The combination of the voltage divider 206 and the low impedance node 207 thus forms a low impedance voltage reference. The low impedance node 207 is connected to the leakage capture conductor 117. In the event that the insulation 116 fails, the leakage capture conductor 117 and low impedance node 207 provide a relatively low impedance path for leakage current from the wire 115 when the AC power signal is high. Accordingly, the leakage current from the wire 115 will be received by the low impedance node 207, which acts as a low impedance current sink, rather than being conducted through tissue to the stimulation electrode $ICI_{1-22}$ that is connected to $V_{SS}$ via a switch 205 and current source 204. When the AC power signal on the wire 115 is low, then the low impedance node 207 acts as a low impedance current source, forming the primary path for current to the wire 115, reducing or substantially eliminating current to the wire 115 through the tissue.

The provision of the low impedance node 207 may both reduce the flow of current through tissue and also reduce distortion in the stimulation signal due to leakage current that would otherwise flow between the insulated cable 113 with failed insulation 116 and the electrodes. Accordingly, if the insulation 116 is breached, for example during surgical implantation or following surgical implantation, the cochlear implant 100 may continue to operate effectively.

In alternative embodiments, the voltage divider 206 and low impedance node 207 may be replaced by another low impedance voltage reference. For example, the low impedance node 207 may be omitted and R2 of FIG. 3 may be replaced with a Zener diode, having a reverse breakdown voltage equal to $V_{ref}$ discussed above. Alternatively, the low impedance node 207 may be retained, with the zener diode providing the voltage reference input to the low impedance node 207. In still other embodiments, a band-gap voltage reference may be used in place of the voltage divider 206 and low impedance node 207.

The current sources 203 and 204 each provide high impedance between the stimulation electrodes $ICE_{1-22}$ and reference electrode $ECE_1$ and the supply rails $V_{SS}$ and $V_{DD}$. This provides an advantage that if the insulation 116 fails, then the interference with the stimulation signal is minimized. If using a single current source, for example, the switching circuit arrangement shown in FIGS. 5 to 7, then there may be increased interference with the stimulation signal in the event of the insulation 116 failing. Another way to provide high impedance between the stimulation electrodes $ICE_{1-22}$ and reference electrode $ECE_1$ and the supply rails $V_{SS}$ and $V_{DD}$ is to provide a 'floating' current source.

For the implant 200 shown in FIG. 2 a similar circuit as shown in FIG. 3 may be used, but without the $ECE_1$.

In some embodiments the leakage capture conductor 217 may perform the dual functions of operating as a reference electrode ECE and as a leakage capture conductor. For example, the leakage capture conductor may function as the reference electrode $ECE_1$ or the reference electrode $ECE_2$ described above with reference to FIG. 1. In these embodiments the leakage capture conductor 217 is provided in electrical communication with tissue, providing a current path from the stimulation electrodes $ICI_{1-22}$ and the leakage capture conductor. In one implementation of these embodiments, an additional electrode $ECE_{2A}$ may be connected to the shield and low impedance node 207, allowing increased flexibility in the physical location of the reference electrode.

While the foregoing description has described the leakage capture conductor 117 as being located to capture leakage current from a cable carrying an AC power signal between implantable modules of a cochlear implant, it will be appreciated that the leakage capture conductor 117 may be located at other locations. For example, the leakage capture conductor 117 may be located about a transfer line in the form of an insulated electrode cable 118 (see FIGS. 1 and 2) that carries stimulation signals from the stimulator module 120, 220 to the stimulation electrodes $ICI_{1-22}$. In these embodiments, while leakage current will be captured, in the event of an insulation breach the operation of the cochlear implant to provide stimulation signals will be affected. In addition, there may be a plurality of leakage capture conductors 117, provided for different parts of the cochlear implant, each connected to the same low voltage node 207 or a plurality of leakage capture conductors may be distributed across a plurality of low voltage nodes. A single part, for example the insulated cable 113 may have one or more associated leakage capture conductors 117.

In addition or as an alternative to capturing leakage current, embodiments of the present invention (e.g., cochlear implants or other medical implants) include an ability to detect leakage current that occurs due to a failure of insulation.

Figure 4:
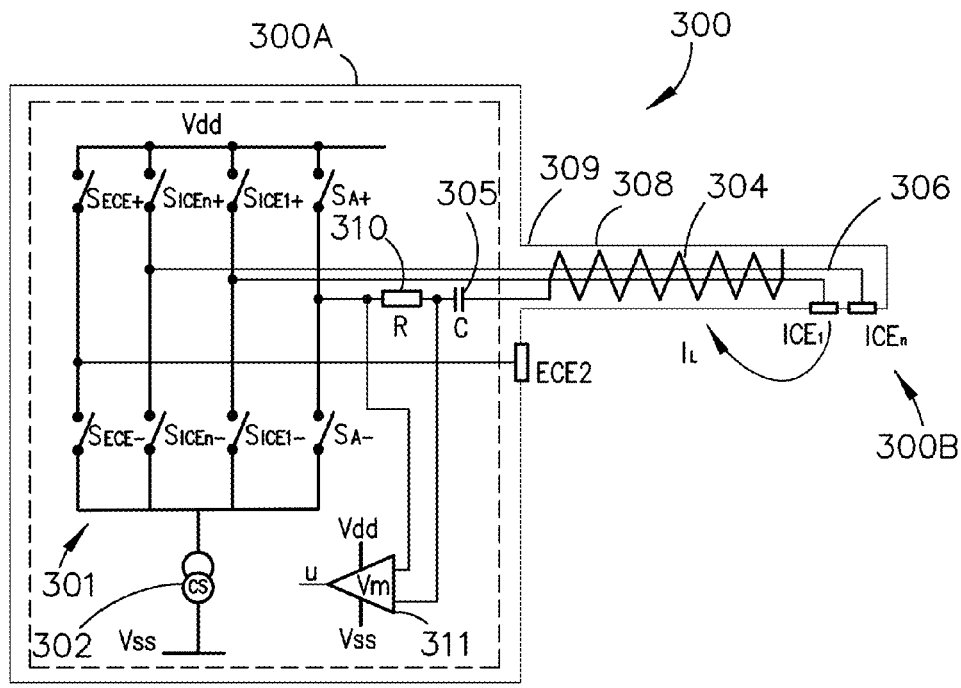
FIG. 4 shows a circuit diagram of a cochlear implant including a leakage current detection circuit in accordance with an embodiment of the present invention.

FIG. 4 shows an embodiment of an implant component 300 of a cochlear implant including a current leakage detection function. Only the functional parts of the implant component 300 directly relevant to embodiment of the present invention illustrated in FIG. 4 are shown. The implant component 300 includes an implantable stimulator 300A and an implantable electrode array 300B. The implantable stimulator 300A includes a switching circuit 301. In the embodiment shown, the switching circuit 301 has a single current source 302, connected to a negative power supply rail $V_{SS}$. In other embodiments, the switching circuit 301 may incorporate a push-pull current source configuration, for example of the form described herein above with reference to FIG. 3 or a floating current source. These other embodiments may have particular application to when leakage current capture through a low voltage node as described herein above is used in combination with the ability to detect leakage current.

The switching circuit 301 includes a pair of switches $S_{ICE(1-n)+}$, $S_{ICE(1-n)-}$ for each stimulation electrode $ICE_1$ to $ICE_n$ and a pair of switches $S_{ECE+}$, $S_{ECE-}$ for a reference electrode $ECE_2$. A further reference electrode (not shown in FIG. 4) to perform the function of the electrode $ECE_1$ shown in FIG. 1 may be provided, particularly if monopolar stimulation is used. In addition, a further pair of switches $S_{A+}$, $S_{A-}$ is provided between $V_{DD}$ and $V_{SS}$, connected to a sensing electrode 304 through a capacitor 305 and a resistor 310. For example, the capacitor may have a capacitance of 100 nF and the resistor a value of 100 kΩ.

An insulated wire 306 connects each stimulation electrode $ICE_{1-n}$ to between a pair of switches $S_{ICE(1-n)+}$, $S_{ICE(1-n)-}$. Insulation 308 is provided about each insulated wire 306. A controller, like the controller 111 (FIG. 1), operates the switches 301 and the current source 302 to achieve a required stimulation signal to the tissue. For bipolar stimulation this is done through the stimulation electrodes $ICE_{1-n}$. For monopolar stimulation electrodes $ICE_{1-n}$ are used together with $ECE_1$ and/or $ECE_2$. A connection point 309 of the cable formed by the wires 306 and insulation 308 may be an insulated connector or the cable may extend into the housing of the implantable stimulator 300A.

The sensing electrode 304 is provided within the insulation 308. The sensing electrode 304 is therefore normally electrically insulated from the tissue, from the wires 306 and from the stimulation electrodes $ICE_{1-n}$. The sensing electrode 304 may be a conductor extending along and within the insulation 308, for example a wire in a coil shape, a mesh extending along the insulated wires 306 or another configuration of conductor extending along and at least over a portion of the insulation 308 where insulation breaches are to be detected. The electrode 304 may be platinum, or another suitable electrically conducting material.

During operation of the implant component 300 to provide signals to the stimulation electrodes $ICE_{1-n}$, the switches $S_{A+}$ and $S_{A-}$ are both open, so that the sensing electrode 304 is disconnected from $V_{DD}$ and the current source 302. The operation of the switching circuit 301 to use the sensing electrode 304 may be performed when the implant component 300 is not providing stimulation signals, for example during a diagnostic phase, which may be performed during power on of the implant component 300 and/or at other times.

With regard to FIG. 4, the first of two test phases will be described. In this phase at least one of the electrodes $ICE_{1-n}$ is connected to $V_{DD}$ by a switch $S_{ICE(1-n)+}$ and the switch $S_{A-}$ is connected to $V_{SS}$ (via the current source 302). The switches $S_{ICE(1-n)-}$ are open. If the insulation 308 is in tact, then there will be a small amount of current between the electrode(s) $ICE_{1-n}$ connected to $V_{DD}$ and the sensing electrode 304 due to capacitive coupling. If on the other hand the insulation 308 has been breached, there will be a relatively low impedance current path through the tissue between the electrode(s) $ICE_{1-n}$ connected to $V_{DD}$ and the sensing electrode 304. The resulting comparatively large leakage current can be readily detected distinguished from the current due to capacitive coupling. In the embodiment shown, the leakage current flows from the electrode(s) $ICE_{1-n}$ connected to $V_{DD}$ to $V_{SS}$ via the sensing electrode 304, the capacitor 305, the resistor 310 and the switch $S_{A-}$. This current may be detected by a voltage detector 311 across the resistor 310. The voltage detector 311 may be a comparator that outputs a logical high when the voltage difference across the resistor exceeds a threshold amount. In other embodiments, the voltage detector 311 may additionally provide an output indicative of a measurement of the magnitude of the leakage current.

In the second of two test phases, at least one of the electrodes $ICE_{1-n}$ is connected to $V_{SS}$ by a switch $S_{ICE(1-n)-}$ and the switch $S_{A+}$ is closed to connect the sensing electrode 304 to $V_{DD}$ (via the capacitor 305 and the resistor 310). The switches $S_{ICE(1-n)+}$ are open. In this test phase, current from the sensing electrode 304 flows to the electrode(s) $ICE_{1-n}$ connected to $V_{SS}$. The voltage detector 311 may be an integrator or comparator to detect both phases, or alternatively may detect current through only one of the phases—the two phases provided to reduce net DC charge being applied to the electrodes over if only a single phase was used. In other embodiments, the test may involve a triphasic switching arrangement or other asymmetrical switching arrangement (this may optionally match the normal switching strategy for the stimulation electrodes). In still other embodiments, when it is acceptable to deliver a net charge to the electrodes, the test may involve just one of the test phases or another unbalanced switching strategy during the test.

After the test phases have been completed, the switches $S_{A+}$, $S_{A-}$ open, disconnecting the sensing electrode 304. The implant component 300 then commences/recommences its functions to provide assisted hearing.

A sensing electrode may be provided in the insulation of a wire to a reference electrode, for example $ECE_1$ shown in FIG. 1, either in addition to or instead of the sensing electrode 304. If both are provided this additional sensing electrode may have its own equivalent to switches $S_{A+}$ and $S_{A-}$, or may share the switches $S_{A+}$ and $S_{A-}$ with the sensing electrode 304. A distinction between these two configurations is that in the earlier of the two breaches of insulation for the ground electrode and stimulation electrodes can be detected separately. Similarly, a sensing electrode may be provided on other transfer lines, for example the transfer line in the form of the cable 113 shown in FIG. 1, either in addition to or instead of the sensing electrode 304 and/or a sensing electrode for $ECE_1$.

If a breach in insulation is detected by the voltage detector 311, then action may be taken in response. For this purpose an output U of the voltage detector 311 may be connected to the controller 111. The actions may include the controller 111 ceasing operation of the implant component 300 and/or the controller 111 setting a flag, which is communicated to an external component that interrogates the implant component 300 to indicate that a breach was detected.

Figure 5:
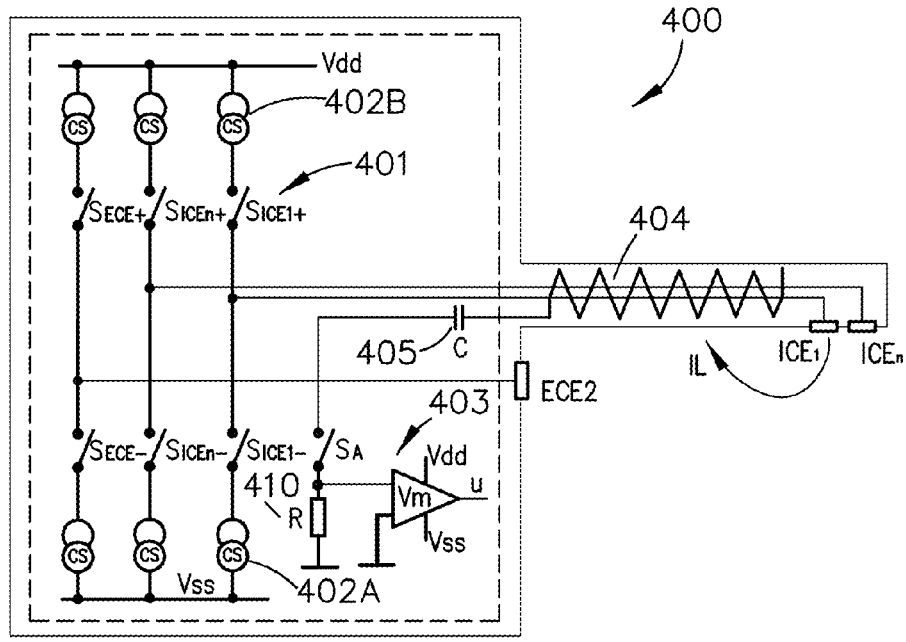
FIG. 5 shows a circuit diagram of a cochlear implant including a leakage current detection circuit in accordance with another embodiment of the present invention.

FIG. 5 shows another embodiment of an implant component 400 of a cochlear implant including a current leakage detection function. Like with FIG. 4, only the functional parts of the implant component 400 directly relevant to the embodiment of the present invention illustrated in FIG. 5 are shown. The implant component includes a switching circuit 401, which includes a pair of switches $S_{ICE(1-n)+}$, $S_{ICE(1-n)-}$ for each stimulation electrode $ICE_1$ to $ICE_D$ and a pair of switches $S_{ECE+}$, $S_{ECE-}$ for a reference electrode $ECE_2$. A further reference electrode (not shown in FIG. 5) to perform the function of the electrode $ECE_1$ shown in FIG. 1 may be provided, particularly if monopolar stimulation is used. A difference to the embodiment shown in FIG. 4 is that the switching circuit 401 is part of a push-pull current source configuration and therefore includes multiple current sources. The implant component includes current sources 402A connected to $V_{SS}$ and current sources 402B connected to $V_{DD}$. The controller of the implant component (e.g. the controller 111 of FIG. 1) switches $S_{ICE(1-n)+}$, $S_{ICE(1-n)-}$ according to a switching strategy (e.g. biphasic or triphasic pulses, monopolar or bipoloar) to provide the stimulation signals to the electrodes $ICE_1$ to $ICE_n$.

A leakage current detection circuit includes a capacitor 405 and a resistor 410, which may have the same values as the capacitor 305 and resistor 310. A voltage detector circuit 403 is provided across the resistor 410. To implement a test phase, the switch $S_A$ is in a closed state simultaneously with one or more of the switches $S_{ICE(1-n)+}$. For a single phase test, the resistor 410 may be connected to a voltage reference $V_{ref}$ that equals $V_{SS}$. In other embodiments, $V_{ref}$ may be at a mid-point between $V_{SS}$ and $V_{DD}$, enabling a second phase of the test, in which $S_A$ remains closed while one or more of the switches $S_{ICE(1-n)-}$ is closed. The mid-point of $V_{ref}$ may be determined the same way as $V_{ref}$ shown in FIG. 3 for the low impedance node 207. An output U indicates the presence of leakage current and this output may be utilised for various actions, for example those described above with reference to FIG. 3.

Figure 6:
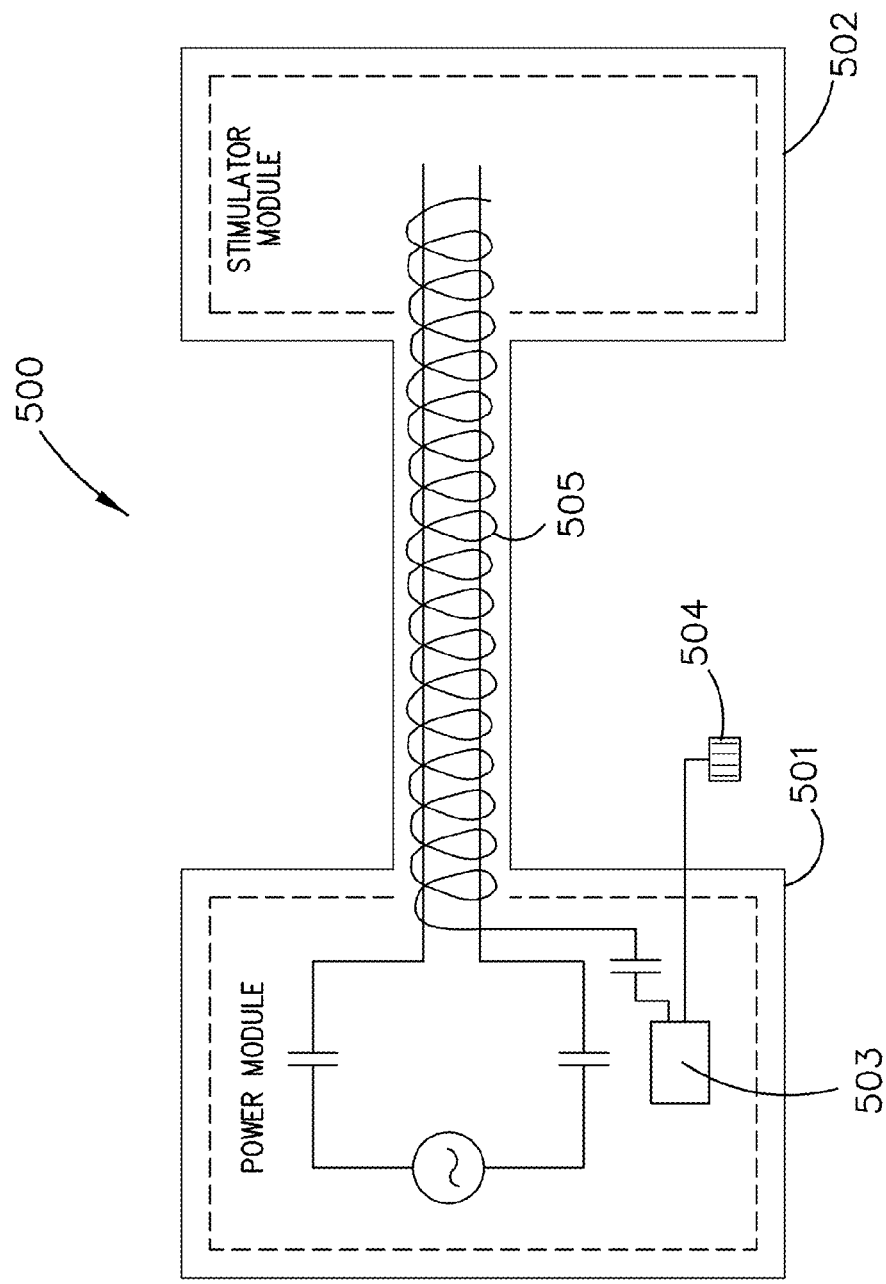
FIG. 6 shows a diagrammatic representation a cochlear implant including a leakage current detection circuit in accordance with another embodiment of the present invention.

FIG. 6 shows another configuration of a cochlear implant with a leakage current detection circuit. The cochlear implant 500 includes a power module 501 and a stimulator module 502, in a like arrangement to that described above with reference to FIGS. 1 and 2. In this example a current detection circuit 503, which may be of the form of the switches $S_{A+}$ and $S_{A-}$ and voltage detector circuit 311 or switch $S_{A+}$ and voltage detector circuit 403 described above in FIGS. 4 and 5 respectively, is provided in the power module 501. The DC power supply to the current detection circuit 503 may be sourced from the battery 102, either directly or via a power supply circuit. For this embodiment the leakage current detection circuit 503 detects failure in insulation of the power transfer line 504, carrying an AC power signal and/or a modulated communication signal. It achieves this by selectively connecting an electrode 504, which is embedded in the tissue, to the positive or negative power terminal of the battery or power supply circuit and measuring current through the sensing electrode 505.

A cochlear implant may be configured to both capture leakage current and detect failure of insulation. Both functions may be provided for the same transfer line.

In some embodiments, the leakage capture conductor 117 is provided as well as the sensing electrode 304. For example, for the same transfer line, the leakage capture conductor 117 may be provided outside of the insulation of the transfer line and the sensing electrode 304 or sensing electrode 404 provided in the insulation.

Figure 7:
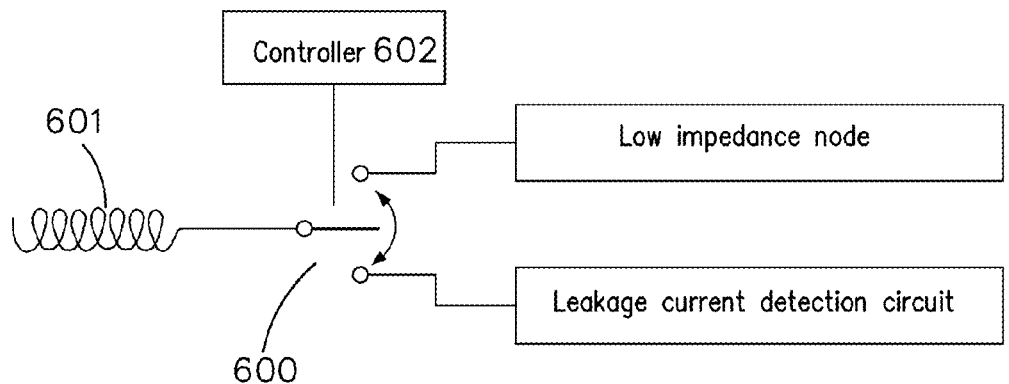
FIG. 7 shows a switching arrangement for providing both leakage current detection and leakage current capture functions in accordance with an embodiment of the present invention.

In other embodiments, as illustrated in FIG. 7, where it is acceptable for the leakage capture conductor 117 to be embedded in insulation, the leakage capture conductor 117 and the sensing electrode 304/sensing electrode 404 may be the same component—leakage capture conductor/sensing electrode 601. In these embodiments, the conductor may be switched between the low impedance node and the leakage current detection circuit. A switch 600, which operates under the control of a microcontroller 602 (which may be the controller 111 of FIG. 1 with functionality to control the switch 600), to selectively connect a leakage capture conductor/sensing electrode 601 to a low impedance node, for example of the type described above with reference to FIG. 3 or to a leakage current detector, for example of the types described above with reference to FIGS. 4 and 5.

In some embodiments, the microcontroller 602 may connect the leakage capture conductor/sensing electrode 601 to the leakage current detection circuit on initialisation of the implant and/or at periodic times for self-diagnosis cycles. At other times, the microcontroller may connect the leakage capture conductor/sensing electrode 601 to the low impedance node.

Figure 8:
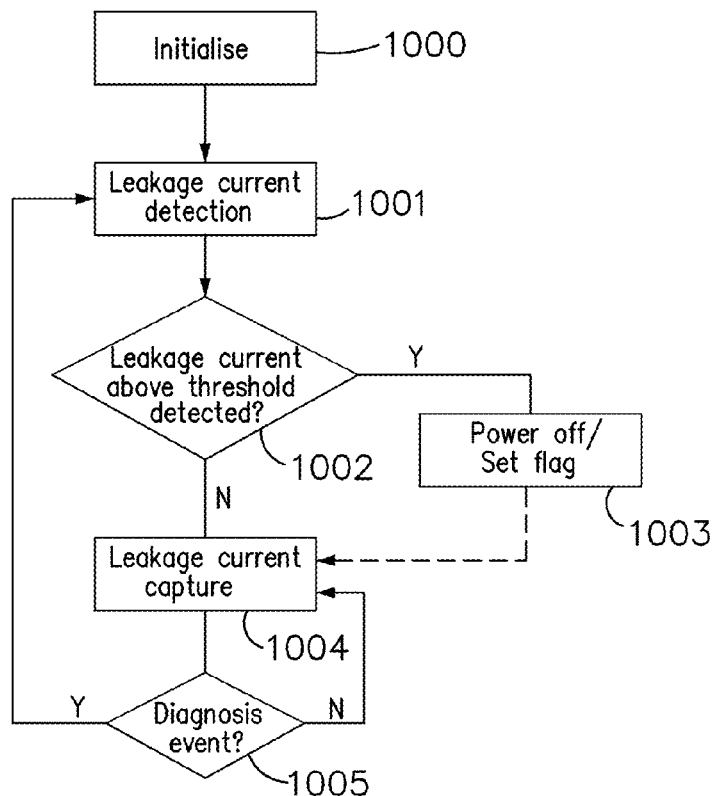
FIG. 8 shows a flow chart of operation of a cochlear implant controller including a leakage capture conductor and a leakage current detection circuit in accordance with an embodiment of the present invention.

FIG. 8 shows a flow chart of a procedure that may be implemented by the controller 111 (see FIG. 1) when both leakage current detection and leakage current capture is provided. In step 1000, the controller 111 is initialised, for example during power-on. A leakage current detection step 1001 is completed by switching the switch 600 to the leakage current detection circuit and by controlled operation of the switches $S_A$ and $S_{ICE}$. The result of the leakage current detection is evaluated (step 1002).

If leakage current above a threshold is detected, the threshold being selected to be at a level higher than expected current due to capacitive coupling, then responsive action is taken in step 1003. This may include powering down the implant, setting a flag to indicate the detection of leakage current for communication to a remote device upon interrogation or another action. Optionally the implant can be designed to continue operating despite the detection of leakage current, in which case the process proceeds to step 1004. Otherwise, the process ends.

If leakage current above the threshold is not detected, the process proceeds from step 1002 to step 1004, with the controller 111 switching the switch 600 to the low impedance node. The switch 600 may remain in this configuration until a diagnosis event occurs (step 1005) and the controller 111 may perform its functions to controllably send stimulation signals to the cochlea via the electrodes ICE during this step. When a diagnosis event occurs, for example the elapsing of a period of time, a certain number of stimulation pulses or other metric, then the process returns to step 1001. If on a first diagnosis event leakage current is detected and on a second diagnosis event leakage current is not detected, then the process may optionally include clearing any flag set in step 1003 between steps 1002 and 1004.

It will be appreciated that a method of producing a medical device implant according to one embodiment of the present invention includes:

providing the medical device with a low impedance node electrically connected to a leakage capture conductor, wherein the low impedance node is configured to maintain the leakage capture conductor at an intermediate voltage between power supply rails of the medical device implant; and configuring the leakage capture conductor to be locatable proximate the exposed insulated conductor.

A controller of the medical device implant may be configured to selectively connect the power supply rails to the electrodes to provide a symmetrical biphasic pulse and the method comprises configuring the low impedance node so that the intermediate voltage is at a mid point between voltages of the power supply rails.

Configuring the leakage capture conductor may comprise providing the leakage capture conductor so that it can be placed in electrical contact with tissue of a recipient when the medical device implant is implanted in the recipient. The controller may provide a monopolar stimulation signal to said electrodes and the method further comprises configuring the medical device so that the leakage capture conductor functions as a reference electrode for the monopolar stimulation signal.

A battery powered AC power supply may be provided for the medical device implant in a first housing and the power supply rails in a second housing. The method may include connecting said exposed insulated conductor to communicate power from the AC power supply between the first housing and the second housing.

It will also be appreciated from the foregoing description that a method of producing a medical device implant of a type that is configured to, under the control of a controller, selectively connect power supply rails to electrodes, includes, according to one embodiment of the invention:

providing, within the insulation of an insulated conductor for carrying electrical charge between component parts of the medical device a sensing electrode, the sensing electrode electrically insulated from both the conductors of the insulated conductor and the and the environment outside the insulation; and providing a connection for said sensing electrode to a current detection circuit operable to detect current between a point of failure of said insulation and an additional electrode, wherein the current detection circuit is configured to provide an output indicative of detection of said current.

The additional electrode may be an electrode that is selectively connected to power supply rails under the control of the controller.

The method may further include configuring the controller to:

selectively connect each of the electrodes to a first power supply rail or a second power supply rail;

selectively connect the sensing electrode to the second power supply rail when said additional electrode is connected to the first power supply rail; and selectively connect the sensing electrode to the first power supply rail when said additional electrode is connected to the second power supply rail.

The method may further include configuring the controller to:

selectively connect each of the electrodes to a first power supply rail or a second power supply rail;

connect the sensing electrode to a voltage reference node at a voltage between voltages if the first and second power supply rails when said additional electrode is connected to the first power supply rail; and connect the sensing electrode to a voltage reference node at a voltage between voltages if the first and second power supply rails when said additional electrode is connected to the second power supply rail.

It will be understood that the invention disclosed and defined in this specification extends to all alternative combinations of two or more of the individual features mentioned or evident from the text or drawings. All of these different combinations constitute various alternative embodiments of the invention.

What is claimed is:

1. A medical device implant comprising:
    stimulation circuitry for providing stimulation signals to electrodes, the stimulation circuitry including one or more power supply rails for providing first and second direct current voltages, respectively;
    an insulated conductor for carrying electrical charge, wherein the medical device implant is structured so that when the medical device implant is implanted in a recipient, insulation of the insulated conductor is in contact with tissue of the recipient;
    a sensing electrode in the insulation; and
    a current detection circuit electrically connectable to the sensing electrode so as to detect current between a point of failure of said insulation and one or more additional electrodes connected to the stimulation circuitry,
    wherein the current detection circuit is configured to provide an output indicative of detection of said current; and
    wherein the stimulation circuitry is configured to selectively connect at least one of the sensing electrode and the one or more additional electrodes to the one or more power supply rails, respectively.

2. The medical device implant of claim 1, wherein the stimulation circuitry further includes first and second power supply rails for providing first and second direct current voltages respectively and controllable switches and is further configured to:
    selectively connect each of the one or more additional electrodes to the first power supply rail or the second power supply rail;
    connect the sensing electrode to the second power supply rail when said additional electrode is connected to the first power supply rail; and
    connect the sensing electrode to the first power supply rail when said additional electrode is connected to the second power supply rail.

3. The medical device implant of claim 1, wherein the stimulation circuitry further includes first and second power supply rails for providing first and second direct current voltages respectively and controllable switches and is further configured to:
    selectively connect each of the one or more additional electrodes to the first power supply rail or the second power supply rail via a current source;
    connect the sensing electrode to a voltage reference node at a voltage between the first and second direct current voltages when said additional electrode is connected to the first power supply rail; and
    connect the sensing electrode to a voltage reference node at a voltage between the first and second direct current voltages when said additional electrode is connected to the second power supply rail.

4. The medical device implant of claim 3, wherein the stimulation circuitry is contained within a first housing, the medical device implant comprises a second housing containing a power source comprising a battery and configured to provide an alternating current power signal, and the insulated conductor is configured to carry the alternating current power signal from the power source to the stimulation circuitry and wherein the medical device implant is configured to selectively connect the one or more additional electrodes to the power source to provide a current flow path through tissue of a recipient of the medical device between the additional electrode and the sensing electrode if the insulation is breached.

5. The medical device implant of claim 1, wherein the sensing electrode comprises a wire or mesh extending along substantially the entire length of the insulated conductor.

6. The medical device implant of claim 1, wherein the current detection circuit provides an output indicative of a magnitude of detected current.

7. The medical device implant of claim 1, wherein the stimulation circuitry is contained within a first housing, the medical device implant comprises a second housing containing a power source for providing an alternating current power signal, and the insulated conductor comprises at least one lead connected to carry the alternating current power signal from the power source to the stimulation circuitry.

8. The medical device implant of claim 7, comprising direct current blocking capacitors in series with the insulated conductor.

9. The medical device implant of claim 1, wherein the insulated conductor is a cable connecting the stimulation circuitry to said electrodes.

10. A method of operating a medical device implant in a recipient, the method comprising:
    communicating an electrical signal over a transfer path of the medical device implant, wherein the transfer path is normally insulated from tissue of the recipient;
    maintaining a sensing electrode about said transfer path, the sensing electrode being insulated from said tissue and said transfer path absent failure of insulation; and
    detecting current from said power transfer path to said sensing electrode due to the failure of insulation there between;
    performing an action in response to said detecting; and
    selectively connecting at least one of the sensing electrode and one or more additional electrodes to one or more power supply rails of the medical device, respectively.

11. The method of claim 10, comprising selectively connecting the sensing electrode to the one or more power supply rails of the medical device.

12. The method of claim 10, further comprising:
selectively connecting each of the one or more additional electrodes for providing stimulation signals to the recipient to a first power supply rail or a second power supply rail;
selectively connecting the sensing electrode to the second power supply rail or the first power supply rail when a said additional electrode is connected to the first power supply rail or the second power supply rail respectively.

13. The method of claim 10, further comprising:
selectively connecting each of the one or more of additional electrodes to a first power supply rail or a second power supply rail;
connecting the sensing electrode to a voltage reference node at a voltage between voltages of the first and second power supply rails when a said additional electrode is connected to the first power supply rail; and
connecting the sensing electrode to a voltage reference node at a voltage between voltages of the first and second power supply rails when a said additional electrode is connected to the second power supply rail.

* * * * *

UNITED STATES PATENT AND TRADEMARK OFFICE
CERTIFICATE OF CORRECTION

PATENT NO. : 8,588,911 B2
APPLICATION NO. : 13/238532
DATED : November 19, 2013
INVENTOR(S) : Nygard et al.

Page 1 of 1

It is certified that error appears in the above-identified patent and that said Letters Patent is hereby corrected as shown below:

In the Claim

Claim 10, column 2, line 58, please delete "said power transfer path" and insert --said transfer path--

Signed and Sealed this
Twenty-fourth Day of December, 2013

Margaret A. Focarino
*Commissioner for Patents of the United States Patent and Trademark Office*